United States Patent [19]

Littleford

[11] 4,357,947
[45] Nov. 9, 1982

[54] ELECTRODE AND METHOD FOR ENDOCARDIAL ATRIAL PACING

[76] Inventor: Philip O. Littleford, 251 Salvador Sq., Winter Park, Fla. 32789

[21] Appl. No.: 168,742

[22] Filed: Jul. 14, 1980

[51] Int. Cl.$^3$ .............................................. A61N 1/04
[52] U.S. Cl. ................................ 128/786; 128/419 P
[58] Field of Search ............................. 128/784–786, 128/419 P, 348, 349 R, 214 R, 642, DIG. 9, 772, 214.4

[56] References Cited

U.S. PATENT DOCUMENTS

| | | | |
|---|---|---|---|
| 3,058,472 | 10/1962 | Thornton, Jr. | 128/348 |
| 3,064,648 | 11/1962 | Bujan | 128/214 R |
| 3,399,668 | 9/1968 | Lundgren | 128/348 X |
| 3,670,727 | 6/1972 | Reiterman | 128/214 R |
| 3,729,008 | 4/1973 | Berkovits | 128/785 |
| 3,757,789 | 9/1973 | Shanker | 128/786 |
| 3,782,381 | 1/1974 | Winnie | 128/349 R X |
| 3,890,977 | 6/1975 | Wilson | 128/785 X |
| 4,154,247 | 5/1979 | O'Neill | 128/419 P |
| 4,198,973 | 4/1980 | Millet | 128/214.4 |
| 4,214,594 | 7/1980 | Little | 128/786 |
| 4,271,847 | 6/1981 | Stokes | 128/786 |

FOREIGN PATENT DOCUMENTS

| 327698 | 6/1903 | France | 128/349 R |
|---|---|---|---|
| 375855 | 7/1907 | France | 128/349 R |

OTHER PUBLICATIONS

Mobin-Uddin et al., "Percutaneous Intracardiac Pacing . . .", J. Thor. Card, Surg., vol. 54, No. 4, Oct. 1967, pp. 545-548.

*Primary Examiner*—Lee S. Cohen
*Attorney, Agent, or Firm*—Duckworth, Allen, Dyer & Pettis

[57] ABSTRACT

A pacing electrode for rapid endocardial insertion for pacing from the right atrium of a patient and for interconnection with a pacemaker includes a flexible conductor having an outer, electrically insulating sheath about the conductor with a flexible curve at one end of the conductor and an exposed terminal along the flexible curved end. The terminal is adapted for making electrical contact with an inner heart surface, preferably within the right atrium. The curved end of the electrode is straightened during insertion through the circulatory system, and thereafter permitted to resume its curved configuration after entering the heart. A wing extends laterally from the sheath at a position outside the patient's body after the curved end has been inserted into the heart. An established relationship between the lateral direction of the wing and the curved end allows the physician to control the orientation of the curved end after insertion to permit the positioning of the electrode in a stable manner within the right atrium, whereby physiological atrial pacing may be achieved.

20 Claims, 6 Drawing Figures

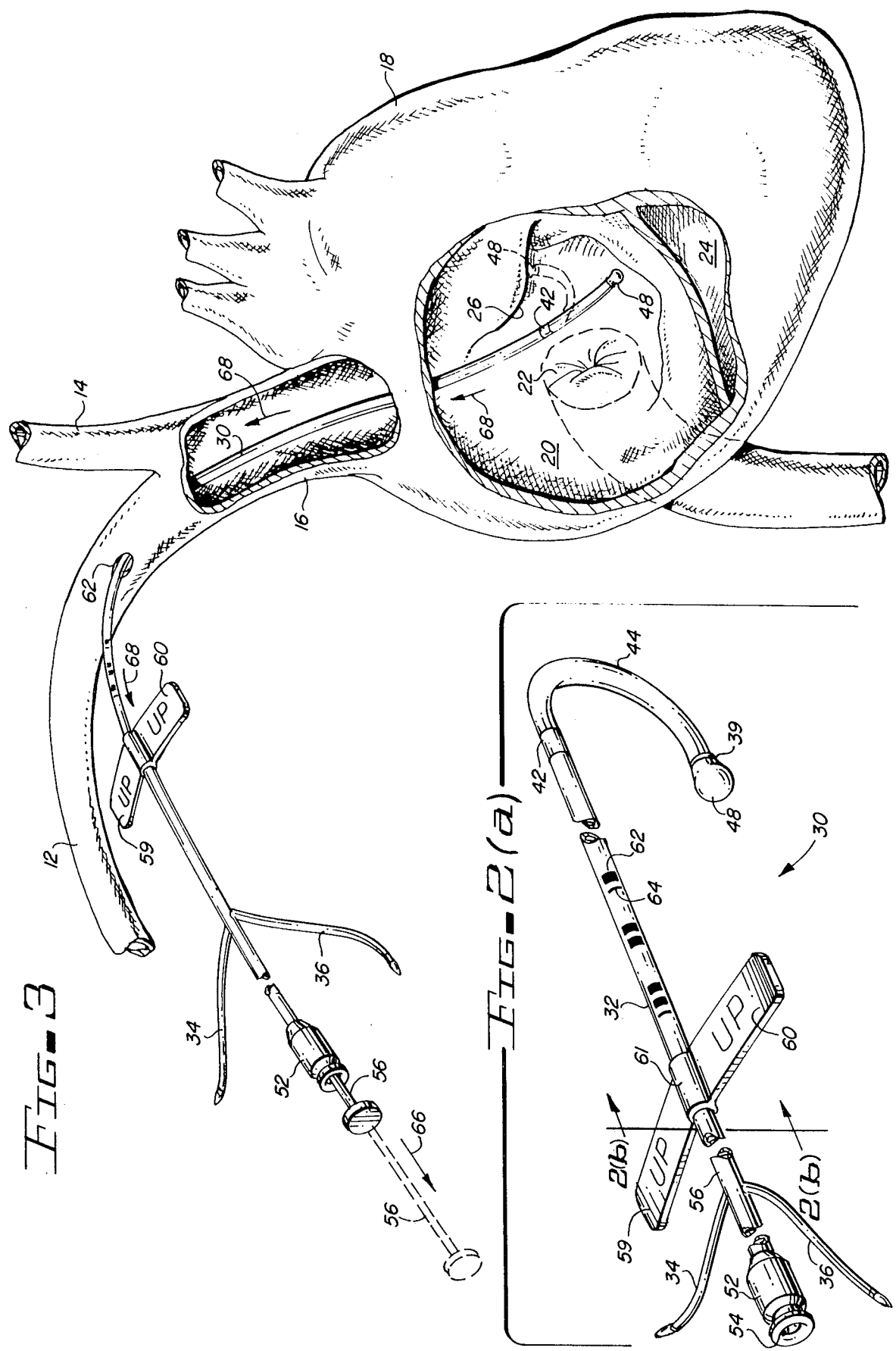

ELECTRODE AND METHOD FOR ENDOCARDIAL ATRIAL PACING

The present invention relates generally to medical and surgical devices and methods, and in particular, relates to electrodes which are designed to be inserted through the circulatory system and into a patient's heart for purposes of permitting an artificial electronic stimuli to pace the patient's heart.

The term "pacemaker" generally applies to a device from a family of electronic products which is electrically connected through an electrode for providing electronic pacing impulses to a patient's heart.

One type of pacemaker, referred to as a permanent pacemaker, is packaged in a small, portable container and is usually implanted under the patient's skin in a major surgical technique. Pacemaker implants are carried out in an operating room or similar facility equipped with a fluoroscope, which permits the attending physician to precisely position the extremity of the permanent pacemaker electrode in a desired location in the heart.

Another type of pacemaker provides temporary pacing stimuli to the patient, and employs an electrode which is designed to be inserted by a physician in a rapid manner while the patient is in an emergency room, intensive care unit, catheter laboratory or similar facility.

Generally, a fluoroscopic unit of some type is used during insertion of a temporary pacing electrode, but occasionally in emergency situations, "blind insertion" has been attempted, but with limited success.

It is well known that the heart may be effectively "paced" by an electronic stimulus located within the right atrium. However, it is very difficult to locate the extremity of an electrode in an appropriate location which is stable in the right atrium, even with the benefit of fluoroscopy. Without the benefit of fluoroscopy (as during the blind insertion of a temporary pacing electrode under the emergency circumstances described above), it has been heretofore unknown to insert a temporary pacing electrode in the right atrium. Because of the inability to effectively locate an electrode within the atrium in a stable manner, most pacing electrodes (both temporary and permanent) are inserted in the right ventricle, which offers stable positioning.

In my U.S. Pat. No. 4,166,469, issued Sept. 4, 1979, I disclose apparatus and a related method for the rapid and atraumatic insertion of pacemaker electrodes through the subclavian vein.

SUMMARY OF THE INVENTION

The present invention contemplates a method and related apparatus for rapidly accurately inserting pacing electrodes, particularly temporary pacing electrodes, into the right atrium. The invention is also based, in part, on the recognition that the insertion through the right subclavian vein of a curved, or "J" electrode into the right atrium will always engage the right atrium in a stable manner when the electrode is oriented and manipulated in a predetermined direction and manner.

More particularly, the electrode of the present invention contemplates a pacing electrode including a flexible conductor having an outer, electrically insulating sheath about the conductor, the conductor and the sheath forming a flexible curve at one end with the conductor having an exposed terminal along the flexible curved end, the terminal adapted for making electrical endocardial contact. Means are further provided along the sheath for indicating the orientation of the curve after the curved end has been inserted into the heart.

In a preferred embodiment of the electrode in accordance with the present invention, the orientation indicating means is dimensioned along the sheath at a position outside the patient's body when the curved end has been inserted through the circulatory system and into the heart. Suitably, the orientation indicating means comprises a wing extending laterally from the sheath, the lateral direction of the wing indicating the orientation of the curved end. One side of the wing is provided with means for indicating which side of the wing should be facing away from the patient. The desired orientation will be obtained in accordance with the present invention when the wing lies flat against the patient's skin, with the "up" indicating means properly positioned.

In accordance with another aspect of the present invention, the electrode includes means for indicating the distance along the sheath from the curved end, permitting the attending physician to first insert the straightened curved end through the circulatory system, manipulating the straightened electrode into the right atrial cavity and permitting the curved end to reform with its extremity pointed toward the right atrial appendage, and thereafter engaging the extremity of the curved end against the right atrial wall in a stable manner by withdrawing the electrode from the circulatory system a distance as determined by reference to the distance indicating means along the sheath. The distance indicating means may be a series of gradations along the outer periphery of the sheath.

DESCRIPTION OF THE DRAWINGS

FIG. 2(a) is a front view, partially cut away, illustrating an electrode in accordance with the present invention.

FIG. 3 is a front view of the human heart, the subclavian and cephalic veins and their connection to the superior vena cava, with portions of the superior vena cava and the heart cut away to illustrate the manner in which the electrode of the present invention is utilized.

DETAILED DESCRIPTION OF THE PREFERRED EMBODIMENT

Figure 1A:
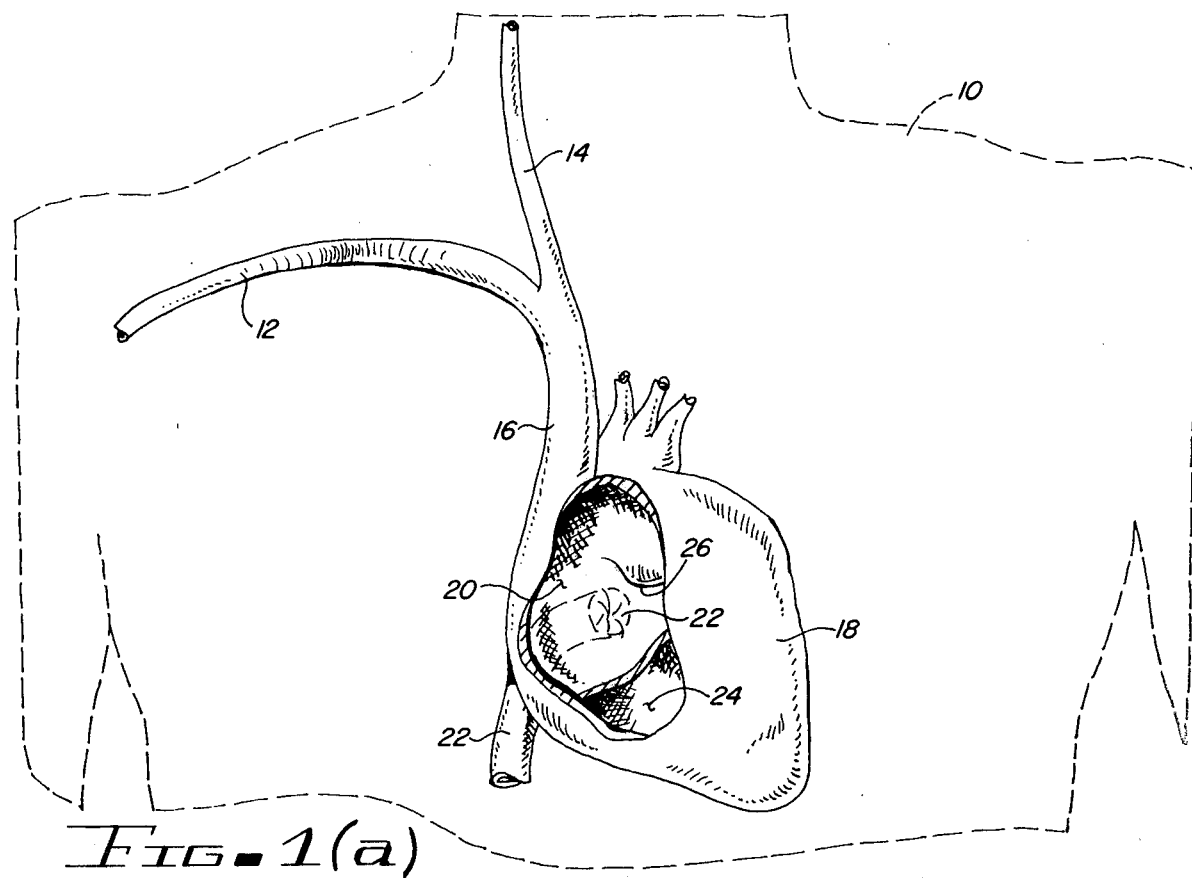
FIG. 1(a) is a front view of the human anatomy, particularly illustrating the human heart with a portion cut away to show the inside of the right atrium and a portion of the right ventricle.

A preferred embodiment of the present invention will now be described with reference to the drawings. While one particular structural arrangement of the electrode in accordance with the present invention is shown in the drawing and described with reference thereto, it will be understood by those skilled in the art from the detailed description set forth below that various modifications may be made in the design of that electrode without departing from the spirit and scope of the present invention.

With particular reference to FIGS. 1(a) and (b), there is illustrated a human body 10, the right subclavian vein 12, the cephalic vein 14 and the superior vena cava 16. The drawing of FIG. 1 is fanciful in nature, it being understood that the drawing is not to scale, but serves only to illustrate the functional relationships of the heart and associated circulatory system.

Element 18 refers to the heart, which includes the right atrium 20, the right ventricle 24, and the inferior vena cava 22. The wall between the right atrium 20 and the right ventricle 24 is cut away in the area where the tricuspid valve would normally be located for purposes of permitting illustration of the right ventricle. As is known, blood from the arms, head, and body flow into the right atrium 20 via the superior vena cava 16 from, among others, the subclavian and cephalic veins 12 and 14. Blood from the trunk and legs enters the right atrium 20 via the inferior vena cava 22.

As is also known, there is a portion of the right atrium known as the right atrial appendage, identified as element 26 in FIG. 1a. The right atrial appendage 26 is a small ear-like appendage forming a pocket located anteriorly and superiorly on the right atrial wall, the inner surface of which is particularly susceptible to pacing.

Figures 1B, 2C:
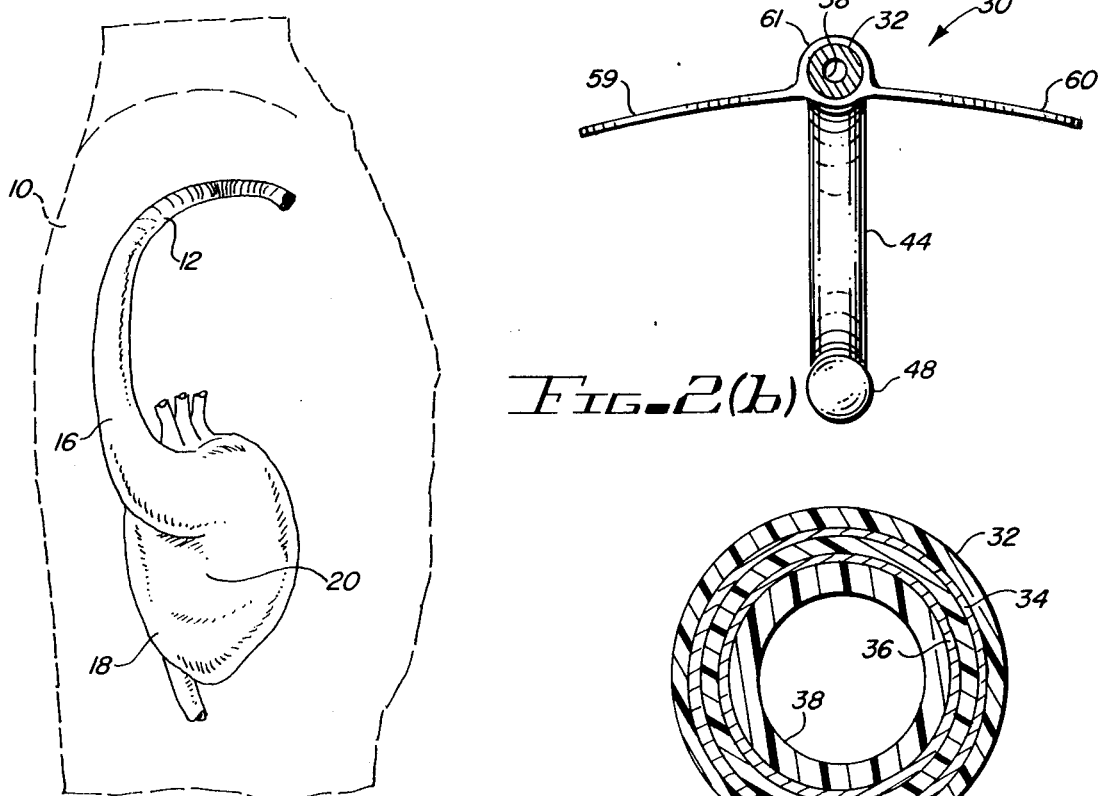
FIG. 1(b) is a side view illustrating a portion of the human anatomy, and specifically illustrating the curvature of the subclavian vein as it enters and connects with the superior vena cava.
FIG. 2(c) is an enlarged illustration of the end section of the view of FIG. 2(b).
Figure 2B:
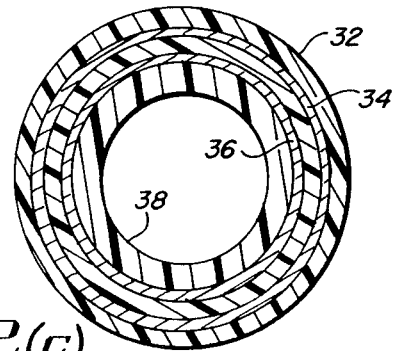
FIG. 2(b) is a front sectional view of the electrode of FIG. 2(a), along the line 2(b)—2(b).

Noting FIG. 1(b), it is seen that the curvature of the subclavian vein to the connection with the superior vana cava 16 is not flat, as it appears in FIG. 1(a), but rather is curved toward the rear of the patient's body, i.e. in the direction toward the spinal column, coming from the forward surface of the body 10.

Reference is now made to FIGS. 2(a), (b) and (c), which disclose a temporary pacemaker electrode in accordance with the present invention.

The electrode, referred to generally by the reference numeral 30, includes a flexible, electrically insulated sheath 32 with a pair of concentric conductors 34, 36 surrounding a central lumen 38 which may, though not necessarily, extend through the electrode 30 to the distal end 39. Each of the conductors 34, 36 are insulated by a layer of insulating material (not numbered—see FIG. 2(c)).

Each of the conductors 34, 36 are exposed at the surface of the outer insulating sheath 32, in order to permit electrical contact in the heart when the electrode 30 is in place. By way of example, conductor 34 may have a surface terminal 42 and inner concentric conductor 36 may have a surface terminal 48 at the distal extremity 39. Typically, the outer conductor 34 will serve to shield the inner conductor 36, and the inner conductor will therefore be relied upon to provide pacing signals at the distal extremity 39 of the electrode 30. In accordance with a preferred embodiment of the present invention, the terminal 48 consists of a spherical conductor connected electrically with the inner conductor 36.

Referring again to FIG. 2(a), the proximal extremity of the electrode 30 includes a hub 52 having an opening 54 which communicates with the central lumen 38. Each of the concentric conductors 34, 36 include external portions which likewise exit the electrode 30 at the proximal end 50, typically in the manner shown in FIG. 2(a). As is well known, the proximal extremities of each conductor 34, 36 may be connected to a temporary pacemaker (not shown).

As is shown on the right-hand side of FIG. 2(a), the electrode 30 is provided with a somewhat gentle curve 44 between the terminal 42 and the distal extremity 39 which permits the conductor terminal 48 at the distal extremity 39 to be pointed in a direction approximately 180°+ from the direction of the electrode 30, and in a plane substantially parallel with the plane of the electrode; that is to say, when the main body of the electrode 30 is lying on a flat surface, the curved portion 44 and the distal extremity 39 are likewise lying in the plane of the same flat surface. The insulative sheath 32, including the insulative materials between the conductive electrodes 34, 36 are of a material which has an elastic memory so that when the curved portion of the distal extremity 39 of the electrode 30 is straightened in the manner hereinafter described, the curved portion at the distal extremity 39 will thereafter resume its curved configuration. A number of conventional silastic and other non-toxic plastic materials are suitable for this purpose.

Straightening of the curve 44 of the electrode 30 may be accomplished by simple manipulation with the hands, or with a stylet having an outer diameter sufficiently small to permit it to pass through the opening 54, down the central lumen 38 to straighten the curved end and hold the entire electrode, including the distal extremity straight. The stylet must be sufficiently flexible to permit the electrode to pass through the subclavian vein 12, the superior vena cava 16 and into the right atrium 20.

In accordance with the present invention, the electrode 30 is provided with means for indicating the relative position of the curved distal extremity 39 with respect to the axial direction of the electrode 30 and the plane in which the electrode and the curved extremity lies. In the embodiment shown in FIG. 2(a), the indicating means in this regard comprises a pair of flat, relatively flexible plastic wings 59, 60 which extend laterally from the outer insulated sheath 32, joined by a sleeve 61. As is shown in FIG. 2(a), the indicating wings 59 and 60 extend generally perpendicular to the plane of the curve 44, the distal extremity 39 and the main body of the electrode 30. As shown in FIG. 2(a) and (b), the wings 59, 60 are curved slightly downward and include the notation "UP" on the upper side intended to be away from the patient's body, as described further below.

The electrode 30 further includes means for indicating the distance along the insulating sheath 32 from the curve in the distal extremity 39. In the embodiment of FIG. 2(a), this distance indicating means comprises a series of gradations along the insulating sheath 32 forward of the indicating wings 59, 60 in the direction of the curve of the extremity 39. Typically, the gradations may include wide gradations 62 and thin gradations 64, each wide gradation indicating a 10 cm. segment and each thin gradation indicating a 5 cm. segment; thus, an individual marking of two wide gradations and one thin gradation would indicate a 25 cm. distance from the curved end.

The manner in which the electrode of the present invention is employed for insertion through the right subclavian vein and into the right atrium without the use of fluoroscopy will now be described with reference to FIG. 3.

Before beginning the technique of inserting the electrode 30 in the manner hereinafter described, the patient is properly prepared and normal sterilization techniques are observed.

Initially, a puncture is made through the patient's skin in the area adjacent the clavicle so as to pass a small, thin-walled 18 gauge needle into the right subclavian vein 12, to thereafter permit the introduction of a removable introducer in the manner which is clearly described in my U.S. Pat. No. 4,166,469. Because the technique for inserting a removable introducer sleeve into the right subclavian vein is clearly described in the specification of that patent, it is incorporated here by reference.

Once that sleeve is properly inserted, the curve 44 of the electrode 30 is straightened. The electrode 30 is then inserted down a removable introducer sleeve (not shown in FIG. 3, but see sleeve 56 in FIG. 11 of my aforementioned U.S. Pat. No. 4,166,469). Once the straightened distal extremity 39 of the electrode is inserted down the introducer sleeve into the subclavian vein 12, it is then manipulated through the superior vena cava 16 and into the right atrium 20. The removable introducer sleeve is then removed by peeling it away, allowing the wings 59, 60 to be positioned close to the entrance site into the subclavian vein 12.

At this point in the technique, the electrode 30 has been inserted as desired so that the straightened distal extremity 39 is positioned in the right atrium 20. It will be understood that the insertion technique thus far described leaves the indicating wings 59 and 60 exteriorly of the patient's skin. As a next step, the attending physician ensures that the indicating wings 59 and 60 are lying substantially parallel to the plane of the patient's skin, and with the words "UP" facing the physician. If a stylet is being used, the stylet is removed. In either event, the curve 44 resumes its normal, curved configuration, as is shown by dotted lines on the right side of FIG. 3.

If the physician has inserted the electrode a sufficient distance into the subclavian vein 12 (and down the superior vena cava 16 and into the right atrium 20), as is determined by reference to the indicating marks 62, 64 along the outer sheath 32, and if the indicating wings 59 and 60 are positioned in the manner described above, then the curved distal extremity 39 will assume a direction in which the terminal electrode 48 is pointed directly upward toward the right atrial appendage 26. This is because of the unique relationship of the curvature from the right subclavian vein 12, running down the superior vena cava 16 and into the right atrium 20, as is clearly shown in FIG. 1(b). As was noted previously, the subclavian vein 12 actually curves slightly backward toward the spinal column as it communicates with the superior vena cava 16, the superior vena cava communicating with the right atrium 20 at the rear of the heart 18. Thus, the indicating wings 59 and 60 and the curvature of the curve 44 are oriented such that when the indicating wings 59 and 60 are positioned substantially parallel to the patient's skin and with the "UP" side facing the physician, then the curve 44 at the distal extremity 39 is formed so that the conductive terminal 48 is pointed in the desired manner in the pocket under the right atrial appendage 26.

Next, the attending physician then pulls the electrode 30 slightly outward away from the puncture wound in the skin and away from the subclavian vein 12, as is shown by the arrows 68 in FIG. 3. The electrode 30 may be withdrawn in this manner a distance of between 1 to 7 centimeters, as determined by reference to the gradations 62, 64 so as to ensure that the conductive terminal 48 engages the surface underneath the right atrial appendage 26. Because of the spherical configuration of the terminal 48, that terminal makes a broad electrical contact with the wall of the right atrium 20 in the pocket of the appendage 26, but without damage to the wall. The terminal 48 stays in the desired location because of the tension at the curve 44, despite continual movement of the atrial wall.

It will be appreciated that the manipulative steps described above can take place without the benefit of fluoroscopy, thus permitting a temporary electrode to be placed easily and quickly into the right atrium 20 for purposes of obtaining the benefits of physiological atrial pacing under emergency or temporary conditions.

I claim:

1. A pacing electrode for rapid endocardial insertion in a patient's body and for interconnection with a pacemaker, comprising:
   (a) a flexible conductor having an outer, electrically insulating sheath about said conductor, said conductor and said sheath forming a flexible curve at one end with said conductor having an exposed terminal along said flexible curved end, said terminal adapted for making electrical endocardial contact;
   (b) means along said sheath for indicating the orientation of said curve after said curved end has been inserted into the heart; and
   (c) said orientation means includes a wing extending laterally from said sheath, the lateral direction of said wing indicating the orientation of said curved end.

2. The pacing electrode recited in claim 1 wherein said orientation indicating means is dimensioned along said sheath at a position distal from said curve at said one end, whereby said orientation means is outside the patient's body when said curved end has been inserted into the heart.

3. The pacing electrode recited in claim 1 wherein said orientation means further comprises means on at least one side of said wing to indicate which side of said wing should be facing away from the patient.

4. The pacing electrode recited in claim 1 wherein said insulating sheath comprises a material having an elastic memory.

5. The pacing electrode recited in claim 1 further comprising means for indicating the distance along said sheath from said curved end.

6. A bipolar pacing electrode for rapid insertion into the heart of a patient and for interconnection with an external pacemaker comprising:
   (a) a pair of electrically insulated flexible conductors;
   (b) an outer, electrically non-conductive flexible sheath around said conductors, said sheath formed of a material having an elastic memory;
   (c) said conductors and sheath forming a flexible curve at one end thereof with said conductors connected with exposed terminals at spaced intervals along the surface of said sheath at said end; and
   (d) means along said sheath and including a wing extending laterally from said sheath for indicating the orientation of said curve after said electrode has been inserted into the heart.

7. The bipolar pacing electrode recited in claim 6 wherein said orientation means comprises:
   (a) the lateral direction of said wing being substantially perpendicular to the orientation of said curved end; and
   (b) means on at least one side of said wing to indicate which side of said wing should be facing away from the patient.

8. The bipolar pacing electrode recited in claim 7 further comprising means for indicating the distance along said sheath from said curved end.

9. The bipolar pacing electrode recited in claim 8 wherein one of said terminals is at the extremity of said curved end, and the other terminal is along said sheath adjacent the point where the curve of said curved end begins.

10. A pacing electrode for rapid endocardial insertion and subsequent orientation to permit pacing the atrium from a pacemaker, comprising:
    (a) a flexible insulated conductor having an elastic curve and a conductive terminal at one end; and
    (b) a wing extending laterally from said conductor at a predetermined position outside the patient's body when said curved end has been inserted into the heart, the lateral direction of said wing indicating the orientation of said curve in the heart, whereby the extremity of said curved end may be engaged against the inner wall of the atrium by appropriate orientation of said wing.

11. The pacing electrode recited in claim 10 further comprising means on one side of said wing for indicating which side of said wing should be facing away from the patient.

12. The pacing electrode recited in claim 10 further comprising means for indicating the distance along said conductor from said curved end.

13. A pacing electrode as recited in claim 10 wherein said conductive terminal further comprises a generally spherical terminal at the extremity of said one end.

14. A temporary pacing electrode for rapid insertion into the heart for pacing the atrium from an external pacemaker, comprising:
    (a) a flexible conductor having an outer, insulative sheath and a curve at the distal extremity, said curve having an elastic memory;
    (b) a conductive terminal at said distal extremity;
    (c) an external terminal at the proximal extremity of said flexible conductor, said external terminal, said flexible conductor and said distal conductive terminal being electrically coupled so as to permit electronic stimuli to be emitted by said conductive terminal when said external terminal is connected to an external pacemaker;
    (d) orientation means coupled to said insulative sheath and including a wing extending laterally from said sheath for providing indicia outside a patient's body of the orientation of said curve when said curve is positioned in the right atrium; and wherein
    (e) appropriate electrical contact between said conductive terminal on the distal end of said conductor and the inner wall of the right atrium is consistently obtained by insertion of said electrode with reference to said orientation means.

15. The temporary pacing electrode recited in claim 14 wherein said orientation means is located a predetermined distance from said curve of said distal extremity.

16. The temporary pacing electrode of claim 14 wherein said insulative sheath at said curve is of an elastic material permitting said curve to be straightened by hand.

17. The temporary pacing electrode recited in claim 14 or claim 16 further comprising means permitting said electrode to be inserted into said heart through the right subclavian vein.

18. A method for rapidly inserting a temporary pacing electrode into the heart of a patient and for orienting the electrode for temporary pacing of the right atrium without fluoroscopy, comprising the steps of:
    (a) providing an electrode having a curve at the distal end with an elastic memory and means including a lateral wing along said electrode for indicating the orientation of said curve;
    (b) straightening the curve;
    (c) introducing said straightened distal end of said electrode through the right subclavian vein, through the superior vena cava and into the cavity of the right atrium of the patient;
    (d) permitting said curve to reform within the right atrium of the patient;
    (e) positioning said orientation means with reference to the lateral direction of said wing during said electrode introduction to orient the extremity of said curved end toward the appendage of the right atrium; and thereafter
    (f) partially withdrawing said electrode a short distance to move the extremity of said curved distal end of said electrode into engagement within the pocket of the right atrial appendage.

19. A method for rapidly inserting a pacing electrode into a patient's body and for orienting an extremity of said pacing electrode with respect to a desired position in the patient's body, said method comprising the steps of:
    (a) providing a pair of lateral wings along said pacing electrode, the lateral direction of said wings indicating the orientation of said extremity;
    (b) introducing said pacing electrode into the patient's body; and
    (c) positioning said wings to orient said extremity in the desired manner.

20. A method for rapidly inserting a pacing electrode into the right atrium of a patient, said method comprising the steps of:
    (a) providing a flexible electrode with an elastic memory and having a curve near the distal end so that said electrode assumes a generally "J" configuration and with a terminal at said distal end, said electrode further including a laterally-extending wing, the lateral direction of which indicates the orientation of said curve;
    (b) straightening said curve and thereafter introducing said electrode into and through the right subclavian vein, the superior vena cava and right atrium with continuous reference to said wing and with the wing parallel to the skin of the patient;
    (c) permitting said curve to reform within the right atrium of the patient; and
    (d) partially withdrawing said electrode to move said terminal into engagement with the right atrium.

* * * * *